United States Patent [19]

Russoniello

[11] Patent Number: 4,860,603
[45] Date of Patent: Aug. 29, 1989

[54] COVECTION COOLING PROBE MOUNTING JACKET

[76] Inventor: Fabio Russoniello, 4520 Stine Rd., Suite 7, Bakersfield, Calif. 93313

[21] Appl. No.: 280,709

[22] Filed: Dec. 5, 1988

[51] Int. Cl.⁴ .............................................. G01L 19/04
[52] U.S. Cl. .................................................... 73/866.5
[58] Field of Search ............ 73/863.11, 864.73, 866.5, 73/23, 27 R

[56] References Cited

U.S. PATENT DOCUMENTS

| | | | |
|---|---|---|---|
| 4,283,947 | 8/1981 | George et al. | 73/863.11 |
| 4,355,539 | 10/1982 | Schatz | 73/863.11 |
| 4,471,664 | 9/1984 | Mailliet et al. | 73/863.11 |
| 4,485,670 | 12/1984 | Camarda et al. | 73/708 |
| 4,756,200 | 7/1988 | Ramsner et al. | 73/864.73 |

Primary Examiner—John Chapman
Assistant Examiner—Michele Simons
Attorney, Agent, or Firm—Jerry N. Lulejian

[57] ABSTRACT

In a hot environment such as the exhaust system of a steam generator an apparatus for protecting a measuring device such as an oxygen concentration probe from heat damage by offering a probe housing within the hot environment for housing the probe and a surrounding convection housing which defines a convection space therebetween substantially closed to the subject environment and open to the ambient environment. The higher temperature of the hot environment relative to the ambient environment causes gas convection currents to flow from the defined convection space to the ambient environment, protecting the probe from heat damage.

16 Claims, 4 Drawing Sheets

COVECTION COOLING PROBE MOUNTING JACKET

BACKGROUND OF THE INVENTION

The present invention relates to an apparatus for protecting devices for measuring some aspect of hot environments against heat damage. The present invention in its preferred embodiment is used to protect oxygen concentration probes from heat damage while they are within exhaust system of steam generators.

In the typical steam generator many feet of piping carries water through the steam generator. The water enters the piping and exits as steam after being exposed to the heat generated within the steam generator. It is highly advantageous for energy conservation purposes to keep the air and fuel mixtures under control to optimize the mix for maximum efficiency in combustion. The steam generator typically includes devices which control the air intake and the fuel intake to the combustion chamber of the steam generator. These devices typically include a digital computer for automatically adjusting the air and fuel mix for optimum efficiency. However, in order for the computer to know the optimum air/fuel mix at any particular time, the computer must be continuously fed information regarding the oxygen concentration in the combustion exhaust.

In order to know the true oxygen concentration of the combustion exhaust without possible contamination from the outside air, measurements of this concentration must be made sufficiently close to the combustion chamber to assure that outside air could not reach the measuring point and result in false measurements. Measurements within the combustion chamber would assure that no outside air would lead to false measurements because of the combustion chamber area is air tight. However, the combustion chamber has operating temperatures of approximately 2500 degrees Fahrenheit. Very few oxygen concentration probes can withstand such temperatures, and, in any event, the ones which can are extremely expensive and become fouled easily because of the concentration of dusty combustion products and gases.

At the flue of the steam generators there is the greatest possibility that outside air would contaminate any measurements of oxygen concentration although this position offers the lowest operating temperature (approximately 400 degrees Fahrenheit). Thus, the flue is completely unsuitable because of the potential for outside air contamination. However, in a median position within the combustion exhaust system prior art measurement systems have found some success in measuring oxygen concentrations without significant outside air contamination. Nevertheless, temperatures ranging from 1400 to 1600 degrees Fahrenheit exist at this median position. Temperatures of 1400 to 1600 degrees Fahrenheit are well over the maximum temperatures that may be withstood by the majority of oxygen concentration probes. Even oxygen concentration probes of the highest temperature ratings in this median position are subject to many other problems that will be discussed below.

In order to reduce the temperature of the combustion gases and products to a level which may be withstood by most oxygen concentration probes, the prior art uses a pipe which circulates combustion gases and products outside the steam generator near the median position. The pipe allows the combustion gases and products to cool significantly before they reach the oxygen concentration probe installed into pipe.

There are many inherent disadvantages of this prior art system for facilitating oxygen concentration measurements. First and most obvious is that by allowing some of the combustion gases and products to cool in the circulation pipe, the steam generator is allowing precious heat energy to be lost. This lost heat energy leads to a less efficient steam generator. Second, the safety of maintenance personnel is greatly compromised by being exposed to hot piping surfaces and to potential rupture or perforation of the pipe and its consequent sudden exposure to high temperature gases and toxic fumes.

Third, the cooling of the combustion gases via the circulation pipe tends to cause highly corrosive condensation products (such as concentrated sulfuric acid) to accumulate in the pipe and around the probe. These products reduce the life of the pipe and probe and add to the danger of injury to maintenance personnel as described above. Fourth, the expense to install and maintain the circulation pipe and the probe is considerable.

The prior art has also attempted to install the probe within the steam generator without the aid of cooling effect of the circulation pipe by placing the probe within a water jacket (unshown) of the type described in U.S. Pat. No. 3,643,508. The description of this water jacket of U.S. Pat. No. 3,643,508 is incorporated herein by reference in its entirety. These water jackets have even more disadvantages than the above described cooling system comprising the circulation pipe. First, the cooling liquid must be pressurized to flow through the jacket. This necessitates expensive and complex pumping apparatus. Second, pressurized cooling liquid is corrosive in nature which means that the system requires continuous maintenance. Third, the temperature of the cooling liquid must be monitored and controlled to avoid over cooling or under cooling. Under cooling will inevitably lead to the boiling away of the cooling liquid and the destruction of the probe. Over cooling can affect the accuracy of the probe and will cause the formation of excessive condensation products around the jacket which are typically highly corrosive. Fourth, the jacket necessarily causes the formation of condensation products which are typically highly corrosive and injurious to the jacket and its installation within the steam generator. The reason for causing the formation of condensation products is that the probe will be cooled below the dew point of the hot gases. Fifth, the jackets are costly to install and maintain.

Other prior art inventions are known which relate generally to protection of probes within hot environments. These are found in U.S. Pat. Nos. 4,668,477; 4,569,228; and 2,122,697. However, no known prior art invention uses convection cooling as does the present invention.

The present invention was created in response to these obvious disadvantages of the prior art systems. As will be shown in the following description of the preferred embodiment, the present invention has successfully eliminated or greatly diminished all of the above described disadvantages.

SUMMARY OF THE INVENTION

The present invention relates to an apparatus which may be used in an enclosed subject environment containing media having an operation temperature higher than the temperature of a substantially gaseous ambient environment and in connection with a probe for measuring some aspect of the subject environment. Such an environment would be the exhaust system of a steam generator.

The present invention is an apparatus for protecting the probe from heat damage and comprises in its general sense (1) a probe housing at least partially within the subject environment for housing the probe and (2) a convection housing at least partially within the subject environment for housing the portion of the probe housing within the subject environment and defining a convection space therebetween which is substantially closed to the subject environment and at least partially open to the ambient environment. The higher temperature of the subject environment relative to the ambient environment causes gas convection currents to flow from the defined convection space to the ambient environment which protects the probe from heat damage.

The present invention may further comprise a means for insulating at least a portion of the convection housing from the subject environment. The amount of insulation preferably is sufficient to maintain the temperature within the probe housing above a dew point of the subject environment. The means for insulating the convection housing preferably comprises refractory insulation around substantially the entire convection housing but not blocking the openness of the probe to the subject environment.

The present invention may also be situated so that liquids therein tend to flow out of the probe housing. This is accomplished in the preferred embodiment by tipping the axis of the probe housing is approximately five (5%) percent below level, which position tends to allow liquids therein to run out of the probe housing. The present invention may also have a means for mounting the probe within the probe housing which comprises a mounting bracket.

In the preferred embodiment, the probe housing and convection housing are generally cylindrical and suspended from each other. The combined probe and convection housings extend transverse and through a wall of conduit defining the subject environment and the convection housing is in a substantially sealed relation to the wall of the conduit. In this preferred embodiment the tip of the mounted probe extends outside the extremity of the probe housing.

DETAILED DESCRIPTION OF THE INVENTION

The present invention relates to an apparatus for protecting measuring devices against heat damage while they are installed in hot environments. The following description of the preferred embodiment of the present invention is discussed in context of its use as mounting jacket for an oxygen concentration probe within a steam generator combustion exhaust environment. This description should not be considered limiting of the uses of the present invention since the present invention may be used to protect any device in any environment containing any media which is at a temperature higher than an ambient environment.

Figure 1:
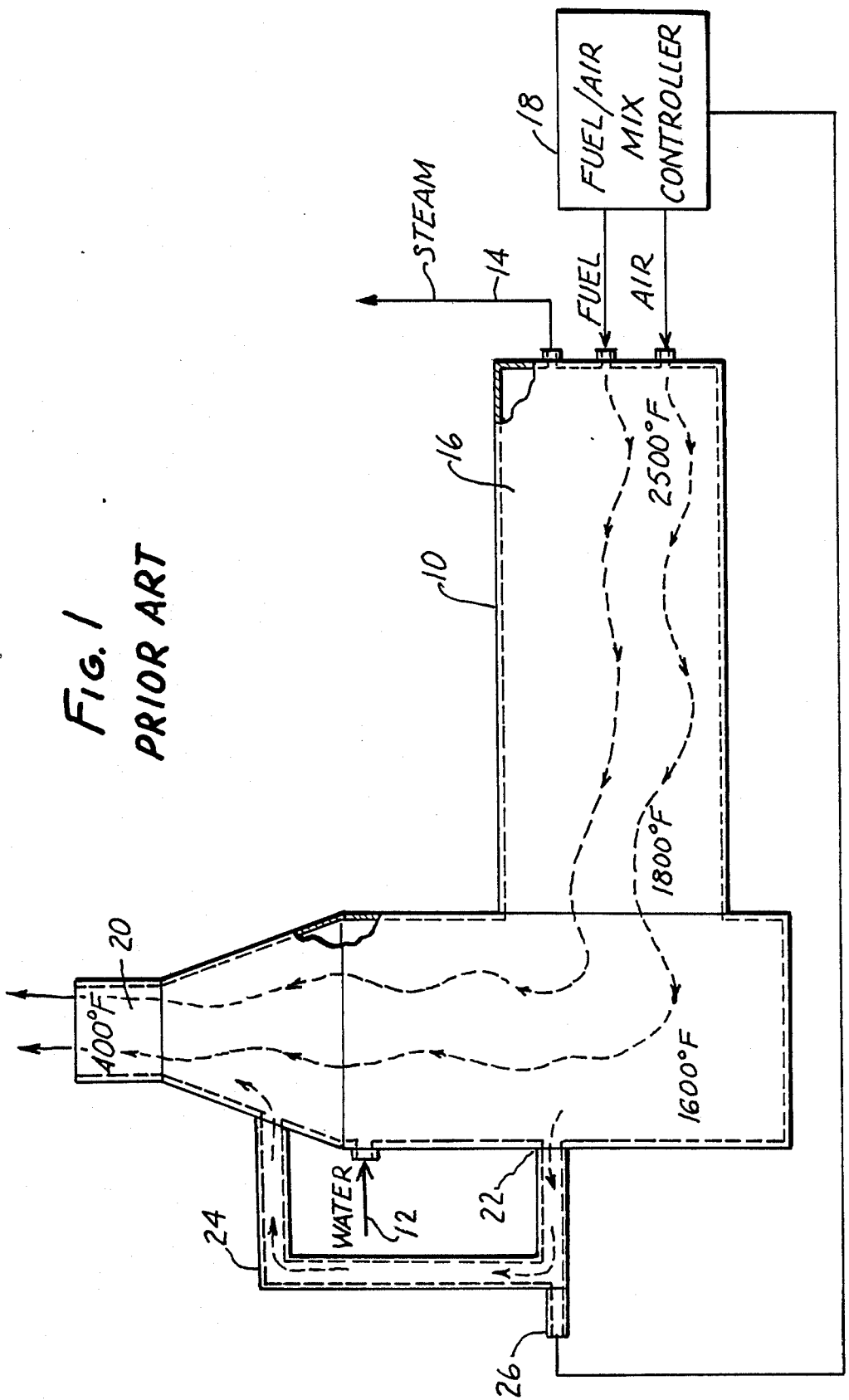
FIG. 1 is a block diagram of a steam boiler with air/fuel mix controllers of the prior art.

Referring specifically to FIG. 1, a typical prior art system for measuring oxygen concentrations in steam generators is shown. The steam generator 10 has many feet of piping (unshown) which carries water through the steam generator 10. The water enters the piping typically at point 12 and exits as steam at point 14 after being exposed to the heat generated within the steam generator 10.

It is highly advantageous for energy conservation purposes to keep the air and fuel mixture under control to optimize the mix for maximum efficiency in combustion. The steam generator 10 typically includes devices 18 which control the air intake and the fuel intake to the combustion chamber 16 of the steam generator 10. These devices 18 typically include a digital computer for automatically adjusting the air and fuel mix for optimum efficiency. However, in order for the computer to know the optimum air/fuel mix at any particular time, the computer must be continuously fed information regarding the oxygen concentration in the combustion exhaust.

In order to know the true oxygen concentration of the combustion exhaust without possible contamination from the outside air, measurements of this concentration must be made sufficiently close to the combustion chamber 16 to assure that outside air could not reach the measuring point and result in false measurements. Measurements within the combustion chamber 16 would assure that no outside air would lead to false measurements because outside air leaks are not present near the combustion chamber. However, the combustion chamber 16 has operating temperatures of approximately 2500 degrees Fahrenheit. Very few oxygen concentration probes can withstand such temperatures, and, in any event, the ones which can are extremely expensive and become fouled easily because of the concentration of particulates in combustion products and gases. At the flue 20 of steam generator 10 there is the greatest possibility that outside air would contaminate any measurements of oxygen concentration. Thus, although the flue 20 position offers the lowest temperature environment (approximately 400 degrees Fahrenheit), it is completely unsuitable because of the potential for outside air contamination. However, in a median position (denoted in FIG. 1 as point 22) prior art measurement systems have found some success in measuring oxygen concentrations without significant outside air contamination.

Nevertheless, temperatures at this median position 22 range from 1400 to 1600 degrees Fahrenheit. Temperatures of 1400 to 1600 degrees Fahrenheit are well over the maximum operating temperatures of the majority of oxygen concentration probes. Even oxygen concentration probes of the highest temperature ratings (which are much more expensive) in this median position 22 are subject to many other problems that will be discussed below.

In order to reduce the temperature of the combustion gases and products to a level which may be withstood by most oxygen concentration probes, the prior art uses a pipe 24 which circulates combustion gases and products from median position 22 and back into flue section 20. Pipe 24 allows the combustion gases and products to cool significantly before they reach oxygen concentration probe 26 which is installed into pipe 24.

There are many inherent disadvantages of this prior art system for allowing oxygen concentration measurements. First and most obvious is that by allowing some of the combustion gases and products to cool in pipe 24, the boiler is allowing precious heat energy to be lost. This lost heat energy leads to a less efficient steam generator 10. Second, the safety of maintenance personnel is greatly compromised by being exposed to high temperature piping 24 and potential rupture or perforation of pipe 24 and the consequent sudden exposure to high temperature gases and toxic fumes.

Third, the cooling of the combustion gases via pipe 24 tends to cause highly corrosive condensation products (such as concentrated sulfuric acid) to accumulate in pipe 24 and around probe 26. These products reduce the life of pipe 24 and probe 26 and add to the danger of injury to maintenance personnel as described above. Fourth, the expense to install and maintain pipe 24 and probe 26 is considerable.

The prior art has also attempted to install probe 26 within steam generator 10 without the aid of the cooling effect of pipe 24 by placing probe 26 directly into the gas stream.

The present invention was created in response to these obvious disadvantages of the prior art systems. As will be shown in the following description of the preferred embodiment, the present invention has successfully eliminated or greatly diminished all of the above described disadvantages.

Figure 2:
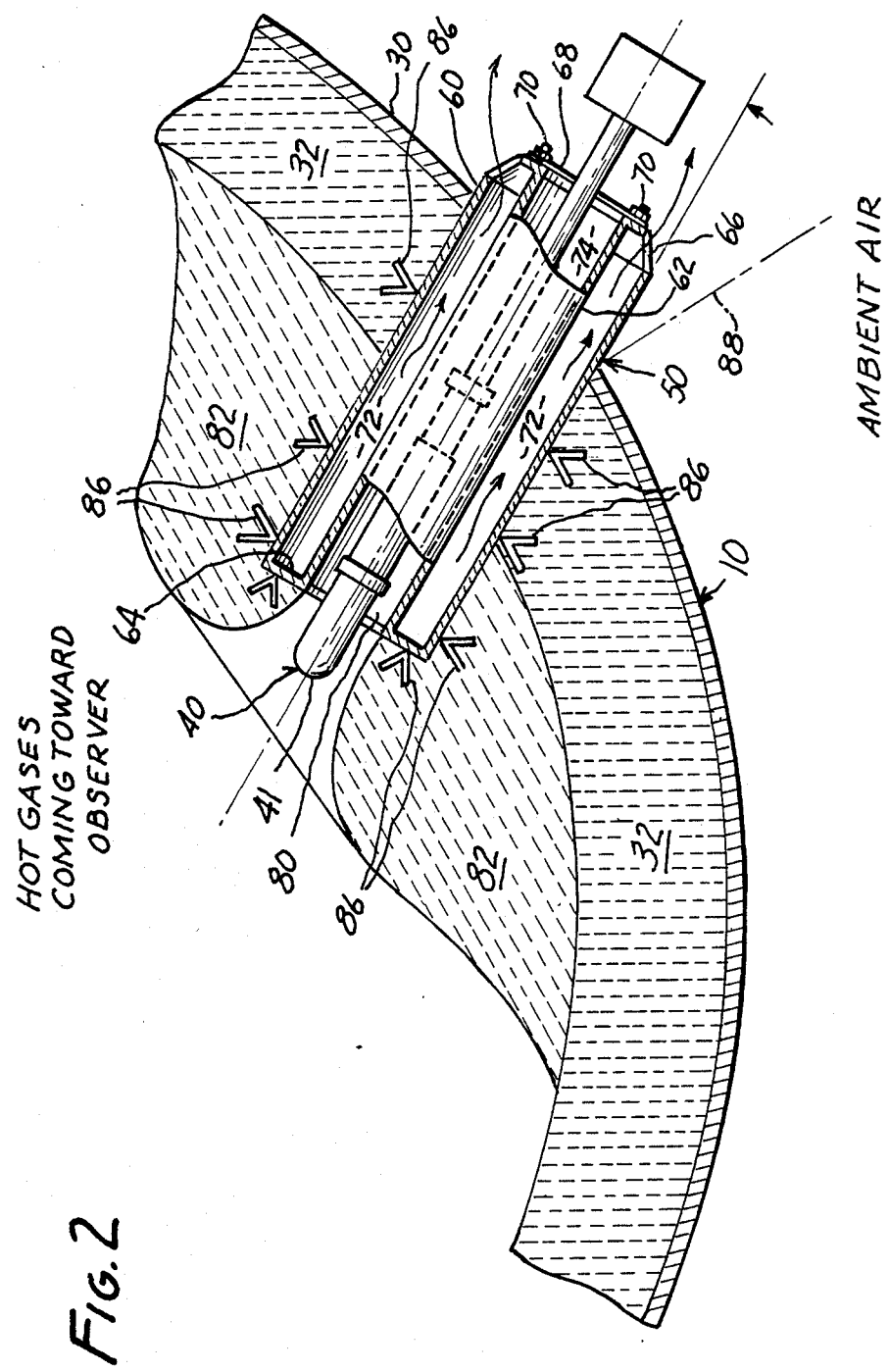
FIG. 2 is a cross-sectional view of the mounting jacket of the present invention installed within the walls of a steam boiler.
Figure 3:
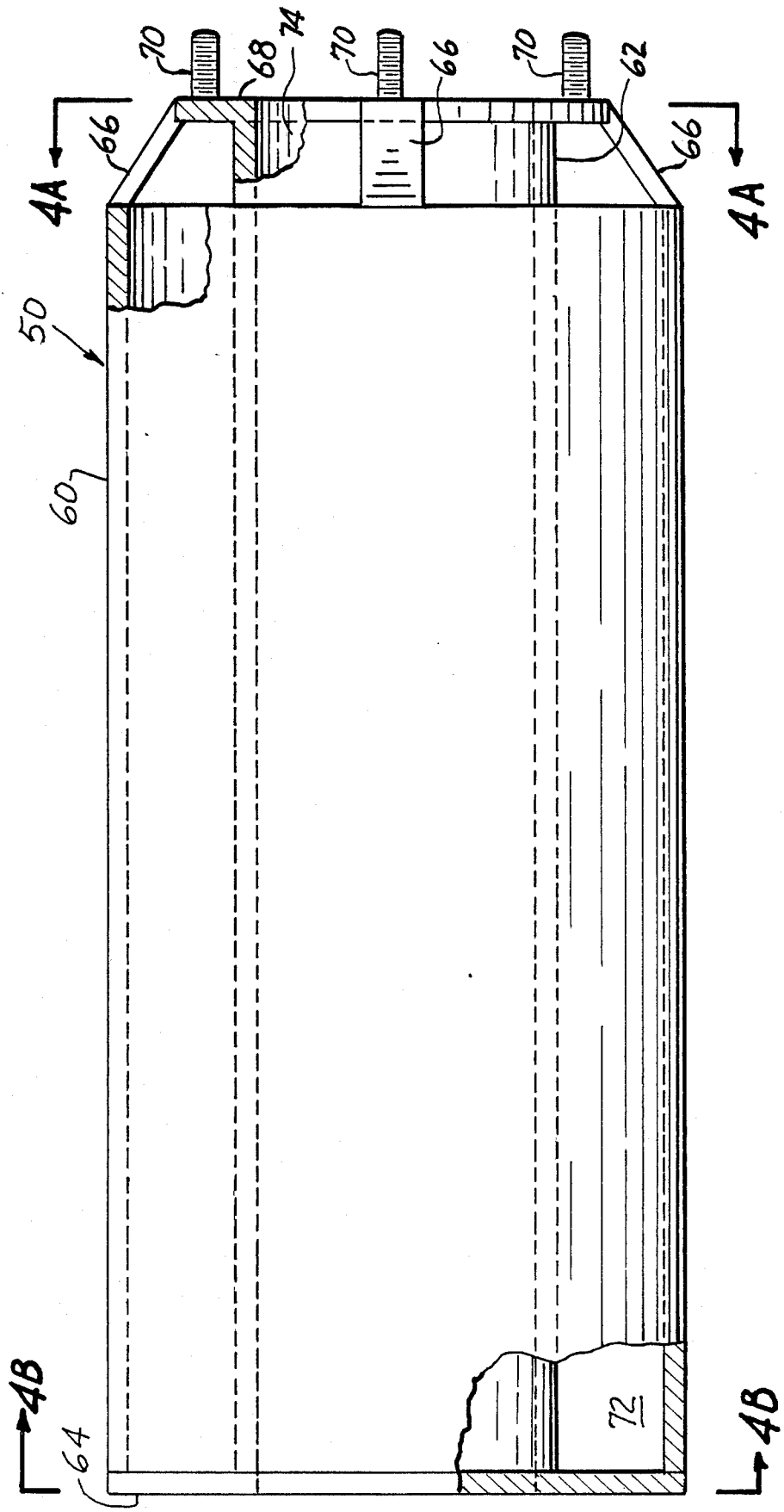
FIG. 3 is a side elevational view of the mounting jacket of the present invention.
Figure 4B:
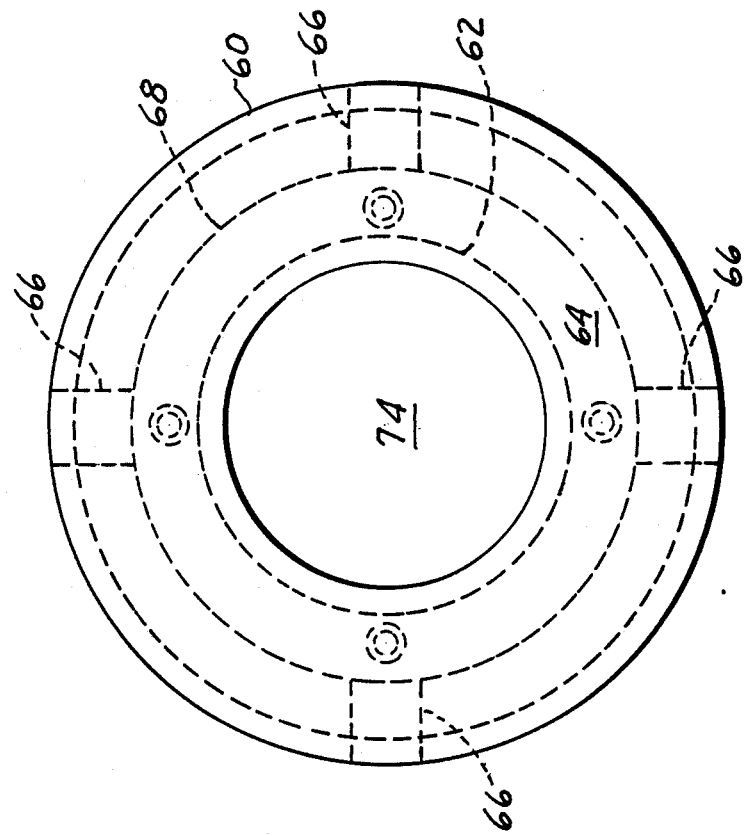
FIG. 4B is a front elevational view of the mounting jacket of the present invention in accordance with line 4B—4B of FIG. 3.
Figure 4A:
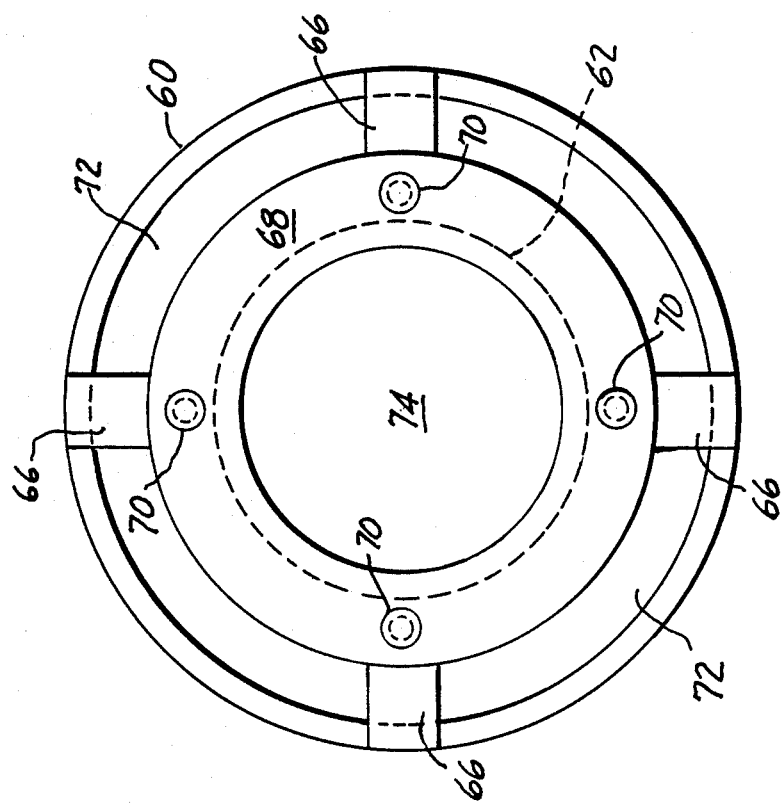
FIG. 4A is an elevational view of the mounting jacket of the present invention in accordance with line 4A—4A of FIG. 3.

Referring specifically to FIG. 2, the present invention in its preferred embodiment is particularly suited for use within a steam generator 10 which typically is constructed of mild steel walls 30 enclosing a ring of castible refractory insulation 32. Within these walls 30 flow hot gases and combustion products as described above for the prior art. In this context the preferred embodiment of the convection mounting jacket 50 of the present invention is mounted through walls 30 at some convenient place on point 22 of FIG. 1. At this location the hot gases and combustion products have a temperature range typically between 1400 and 1600 degrees Fahrenheit.

The probe 40 may be an oxygen concentration sensor of the type sold by Westinghouse Electric Corporation of Orrville, Ohio under Model Numbers 132, 218, or 225. However, these are simply suggested oxygen concentration sensors, and it must be kept in mind that any type of probe or sensor may be used with the present invention. These suggested sensors have maximum process temperature specifications of between 1000 and 1400 degrees Fahrenheit and cost approximately four (4) times less than similar sensors which can withstand temperatures in excess of 1500 degrees Fahrenheit such as Westinghouse Model 450. One of the benefits of the present invention is that these lower priced sensors may successfully be used in high temperature applications and without the disadvantages outlined above for the prior art systems.

Referring to FIGS. 2, 3, 4A and 4B, the convection mounting jacket 50 of the preferred embodiment of the present invention is comprised of a generally cylindrical outer housing 60, generally cylindrical inner housing 62, a doughnut shaped cap piece 64, mounting flanges 66 and mounting bracket 68 with its mounting bolts 70. The inner and outer housings 62 and 60 define a convection space 72. The inner housing 62 defines a probe housing space 74 to house the probe to be protected.

In context of the use of the preferred embodiment in a steam boiler in working temperatures of between 1400 and 1600 degrees Fahrenheit, the outer housing 60 is preferably constructed of six (6") inch schedule 40 A106 steel pipe. The inner housing 62 is constructed of three (3") inch schedule 40 330 alloy steel pipe. The cap piece 64 is constructed of one quarter (¼") inch 316 or 330 plate steel and extends between and is welded along intersection of the cap piece 64 and the extremities of the inner and outer housings 62 and 60. Mounting flanges 64 and mounting bracket 68 are constructed of one quarter (¼") inch A36 steel. The mounting bolts 70 are preferably five-sixteenth (5/16") inch, eighteen (18) thread per inch bolts, each three quarter (¾") inch long. The mounting flanges 64 are welded to the outer housing 60 and the mounting bracket 68 in the positions shown in FIGS. 3, 4A and 4B. The inner housing 62 is welded to the mounting bracket 68 where the extremity of the inner housing 62 and the mounting bracket 68 meet. The result of the aforementioned construction is the defining of the mentioned convection space 72 and probe housing space 74. The probe 40 may be mounted to the mounting bolts 70 of the mounting bracket 68 with the appropriate hardware.

The mounting jacket 50 is mounted within walls 30 by cutting a hole therein just wide enough to allow the outer housing 60 to fit therethrough. The mounting jacket 50 is welded to walls 30 around the circle defined by the border between the outer housing 60 and the walls 30 to create an air tight seal and to securely mount the mounting jacket 50.

The convection space 72 is substantially closed to the hot gaseous environment within walls 30 (FIG. 1), but open to the ambient environment via the spaces between the mounting flanges 66. When the mounting jacket 50 of the preferred embodiment is installed within walls 30 as shown in FIG. 1 and because the environment within walls 30 is at a higher temperature than the ambient environment, convection air currents within the convection space 72 draw heat away from the probe housing space 74 by the operation of the rising hot air which exits to the ambient environment through the spaces between the mounting flanges 72 and the incoming cool air. This convection action cools the probe housing space 74 significantly and may alone be all that is necessary to cool probe 40 (FIG. 1) to temperatures within its maximum process temperature.

In the preferred embodiment of the mounting jacket 50, it is desired to prevent cooling of the probe housing space 74 to temperatures at or below the dew point for the range of temperatures presented during combustion. This is to prevent condensation within the probe housing space 74, around the outer housing 60 and on probe 40. As previously described, condensation products of combustion are highly corrosive and must be avoided.

The typical steam generator 10 (FIG. 1) has within walls 30 a ring 32 of castible refractory insulation of any of a number of kinds. In order to limit the amount of heat loss from the steam generator 10 and to avoid the formation of condensation, it is preferred to limit the amount of insulation surrounding the outer housing 60.

The outer housing 60 is surrounded (but preferably not the entrance 80 to the probe housing space 74) with castible refractory insulation 82 of the same type as comprises insulation ring 32. The amount of insulation 82 to use will depend on the temperature range of the environment within walls 30 and the dew point of the hot gases therein. Some experimentation will be necessary for each application to assure that the temperature within the probe housing space 74 is never at or below the dew point during operating conditions. However, the insulation 82 should be tied around the outer housing 60 with appropriate insulation hangers 86 to prevent it from being removed or loosened by the stream of hot gases.

The probe tip 41 may be allowed to jut out of the entrance 80 to the probe housing space 74 and may allow hot gases to pass around probe 40 within the probe housing space 74. However, the entrance 80 may also be sealed around the probe tip 41 with an appropriate high temperature material (unshown) if extra heat insulation of the probe 40 is desired.

In the preferred embodiment the mounting within walls 30 tips the mounting jacket 50 at five (5) degrees below a line 88 representing level (at right angles to the plumb). This position is to allow any possible condensation products which form within the probe housing space 74 to run out and away from mounting jacket 50.

As can be seen from the preceding discussion, the disadvantages of the prior art systems have been eliminated or greatly diminished. Specifically, the need to bypass some of the hot gases from the boiler or other hot environment is eliminated along with its consequent heat loss, safety concerns and high installation and maintenance costs. Condensation products are almost entirely eliminated. The need for high temperature probes is eliminated along with their extremely high cost and potential for fouling. The need for pressurized cooling liquids with their consequent internal and external corrosive effects, complex pumping and temperature control apparatus and high installation and maintenance costs is eliminated.

The preceding discussion of the preferred embodiment of the present invention is for illustrative purposes only and should not be considered as limiting the scope of the present invention. Instead, the scope of the present invention shall be determined by the following claims and their equivalents.

I claim:

1. In an enclosed subject environment containing media having an operation temperature higher than the temperature of a substantially gaseous ambient environment in connection with a probe for measuring some aspect of the subject environment, an apparatus for protecting the probe from heat damage comprising:
    a probe housing at least partially within the subject environment for housing the probe;
    a convection housing at least partially within the subject environment for housing the portion of the probe housing within the subject environment and defining a convection space there between which is substantially closed to the subject environment and at least partially open to the ambient environment through areas defining openings from the defined convection space to the ambient environment which are adapted to substantially allow the free flow of gases between the defined convection space and the ambient environment;
    the higher temperature of the subject environment relative to the ambient environment causing gas convection currents to flow from the defined convection space to the ambient environment and protecting the probe from heat damage.

2. The apparatus in accordance with claim 1 further comprising a means for insulating at least a portion of the convection housing from the subject environment.

3. The apparatus in accordance with claim 1 in which the probe housing is situated so that liquids therein tend to flow out of the probe housing.

4. The apparatus in accordance with claim 1 in which the probe is partially housed by the probe housing and the probe housing is open to the subject environment.

5. The apparatus in accordance with claim 1 further comprising a means for mounting the probe within the probe housing.

6. The apparatus in accordance with claim 1 further comprising:
    a means for insulating at least a portion of the convection housing from the subject environment; and
    a means for mounting the probe within the probe housing.

7. The apparatus in accordance with claim 6 in which the probe housing is situated so that any liquids therein flow out of the probe housing.

8. The apparatus in accordance with claim 7 in which the probe is partially housed by the probe housing and the probe housing is open to the subject environment.

9. The apparatus in accordance with claim 6 in which the means for insulating the convection housing comprises refractory insulation around substantially the entire convection housing but not blocking the openness of the probe to the subject environment.

10. The apparatus in accordance with claim 9 in which the means for mounting the probe within the probe housing comprises a mounting bracket.

11. The apparatus in accordance with claim 9 in which the subject environment and the ambient environment are defined by a conduit having a wall which contains the media of the subject environment, the probe housing and convection housings are generally cylindrical and suspended from each other, the combined probe and convection housings extend transverse and through the wall of the conduit and the convection housing is in a substantially sealed relation to the wall of the conduit.

12. The apparatus in accordance with claim 11 in which the mounted probe extends outside an extremity of the probe housing.

13. The apparatus in accordance with claim 12 in which an axis of the probe housing is tipped approximately five (5%) percent below level, which position tends to allow liquids therein to run out of the probe housing.

14. The apparatus in accordance with claim 13 in which the combined probe and convection housings are substantially surrounded by a refractory insulation but the portion of the probe which extends outside the extremity of the probe housing is left uninsulated from the subject environment.

15. The apparatus in accordance with claim 14 in which the probe is mounted within the probe housing by its interconnection to a mounting bracket.

16. The apparatus in accordance with claim 2 in which the amount of insulation is limited to an amount which will maintain the temperature within the probe housing above a dew point of the subject environment.

* * * * *